(12) United States Patent
Zgonis et al.

(10) Patent No.: US 8,764,750 B2
(45) Date of Patent: Jul. 1, 2014

(54) FOOT, ANKLE AND LOWER EXTREMITY COMPRESSION AND FIXATION SYSTEM AND RELATED USES

(75) Inventors: Thomas Zgonis, San Antonio, TX (US); Heather Hanson, San Antonio, TX (US); George Lamberson, San Antonio, TX (US); Jeffrey Harris, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 461 days.

(21) Appl. No.: 13/063,241

(22) PCT Filed: Sep. 11, 2009

(86) PCT No.: PCT/US2009/056756
§ 371 (c)(1),
(2), (4) Date: Jun. 21, 2011

(87) PCT Pub. No.: WO2010/030960
PCT Pub. Date: Mar. 18, 2010

(65) Prior Publication Data
US 2011/0245830 A1  Oct. 6, 2011

Related U.S. Application Data

(60) Provisional application No. 61/096,102, filed on Sep. 11, 2008.

(51) Int. Cl.
*A61B 17/00* (2006.01)
(52) U.S. Cl.
USPC .......................................................... 606/57

(58) Field of Classification Search
USPC ........... 606/54–60, 67, 68, 280, 71, 282–286, 606/294, 90, 102, 105, 300
See application file for complete search history.

(56) References Cited

U.S. PATENT DOCUMENTS

| | | | |
|---|---|---|---|
| 6,537,274 B1 | 3/2003 | Katz | |
| 6,682,563 B2 | 1/2004 | Scharf | |
| 7,094,236 B2 | 8/2006 | Waisman | |
| 2004/0068187 A1 | 4/2004 | Krause et al. | |
| 2004/0138659 A1* | 7/2004 | Austin et al. | 606/54 |
| 2005/0059968 A1 | 3/2005 | Grant et al. | |
| 2006/0184083 A1 | 8/2006 | Buckman et al. | |
| 2006/0206044 A1 | 9/2006 | Simon | |

OTHER PUBLICATIONS

International Search Report mailed Feb. 3, 2010; Authorized Officer: Lee W. Young.

\* cited by examiner

*Primary Examiner* — Pedro Philogene
*Assistant Examiner* — David Comstock
(74) *Attorney, Agent, or Firm* — Winstead PC

(57) ABSTRACT

The present devices, systems and processes can simultaneously reduce a malady of the foot, ankle, and/or lower extremity and provide compression and stabilization through the use of a combined internal fixation device, external fixation device and a lower extremity stabilizing device. The various embodiments of the system are capable of providing adequate compression in the medial, central and/or lateral columns and/or sides of the foot, ankle, and/or lower extremity, as well as treating Charcot neuroarthropathy, fractures, revisional foot and combination of ankle surgeries. The external fixation device and/or lower extremity stabilizer can be removed after a certain period of time, leaving the internal fixation system within the body for prolonged stabilization and maintenance of the arthrodesis site(s).

17 Claims, 7 Drawing Sheets

FIG. 3B  FIG. 3C

FOOT, ANKLE AND LOWER EXTREMITY COMPRESSION AND FIXATION SYSTEM AND RELATED USES

CROSS-REFERENCE TO RELATED APPLICATIONS

This application claims priority to U.S. Provisional Patent application Ser. No. 61/096,102, filed Sep. 11, 2008, which is incorporated by reference herein in its entirety.

STATEMENT REGARDING FEDERALLY SPONSORED RESEARCH

Not applicable.

BACKGROUND

There are about 26 bones in the human foot (about 28 if you include the sesamoid bones at the base of the big toe). These are: 1) the talus, which connects to the tibia and fibula at the ankle; 2) the calcaneus, which forms the heel; 3) the navicular, cuboid, and three cuneiforms (medial, intermediate, and lateral), which form the middle of the foot; 4) the five metatarsals, which radiate out to the toes; and 5) the 14 phalanges (2-3-3-3-3), which form the toes.

The joint named "ankle" is made up of the tibia, the fibula, and the talus. Below the talus is another joint called the "below the talus joint" or, in another language, the subtalar joint. That joint between the talus and calcaneus is intricately inseparable from the action of the midfoot and rearfoot joints.

Charcot neuroarthropathy (CN) is defined by a bone and/or joint deformity in limbs that have lost sensory innervation. The incidence is very high in diabetic patients with peripheral neuropathy. Currently, the pathogenesis of CN is largely unknown. This is often reflected in that diabetic patients with CN present challenging surgical candidates secondary to diabetes-related complications.

CN is a progressive disorder believed to result from a disturbance in pain and sensation as a result of peripheral neuropathy. Originally described as a complication of syphilitic neuropathy, the Charcot foot and ankle in the last decade has been most commonly associated and treated in patients with uncontrolled diabetes mellitus and dense peripheral neuropathy. The true etiology and nature of this debilitating condition is still unknown, and the treatment is variable and patient-dependent. Historically, foot and ankle deformities as a result of CN were treated with immobilization, total contact casting and, later, with accommodative footwear or bracing. Unfortunately, the evidence supporting non-operative treatment for the Charcot foot is equivocal. The increased risk of amputation in the non-operative treatment of CN should alert the treating physician to use caution and close monitoring in the presence of a severe deformity, fracture/dislocation, instability, and/or ulceration. Currently, the literature has shown variable protocols, techniques, and outcomes for surgical reconstruction of these complex and debilitating deformities, raising great concerns on the treatment options for the Charcot foot and ankle.

The presence of ulceration, severe osseous deformity, poor bone quality, neuropathy, immune deficiency, obesity and multiple co-morbidities commonly seen in this patient population limit the use of traditional internal fixation to achieve a successful outcome. The risk of surgical infection is increased in diabetics due to their impaired immune system. In the presence of ulceration with an underlying bony prominence, this risk of infection and future amputation is high, and the ability to utilize internal fixation alone is limited. Accordingly, CN involving severe deformity, instability, ulceration, and/or infection of the foot and/or ankle poses difficulty in achieving limb salvage. When the surgeon is faced with this clinical scenario, limb salvage is often plausible through a rationale approach that, in various treatments, incorporates arthrodesis of affected joints to correct the deformity, plastic soft tissue reconstruction for wound closure, and application of an external fixation device.

Generally, arthrodesis has been used to artificially induce joint ossification between two bones via surgery. A bone graft can be created between the two bones using a bone from elsewhere in the person's body (autograft) or using donor bone (allograft) from a bone bank.

Bone autograft is generally preferred by surgeons because, as well as eliminating the risks associated with allografts, bone autograft contains native bone-forming cells (osteoblasts), so the graft actually forms new bone itself (osteoinductive); it acts as a matrix or scaffold to new bone growing from the bones being bridged (osteoconductive). The main drawback of bone autograft is the limited supply available for harvest.

Bone allograft has the advantage of being available in far larger quantities than autograft; however, the treatment process the bone goes through following harvest, which usually involves deep-freezing and may also involve demineralization, irradiation and/or freeze-drying, kills living bone or bone marrow cells. This significantly reduces the immunogenicity (risk of graft rejection) such that no anti-rejection drugs are needed and, combined with appropriate donor screening practices, these processing and preservation practices can significantly reduce the risk of disease transmission. In spite of all of this processing, cancellous allograft bone retains its osteoconductive properties. Furthermore, certain processing practices have been shown to also retain the acid-stable osteoinductive proteins in cortical bone grafts so that many bone allografts can be considered both osteoconductive and osteoinductive.

Likewise, a variety of synthetic bone substitutes are commercially available. These are usually hydroxyapatite-based granules formed into a coralline or trabecular structure to mimic the structure of cancellous bone. Such materials can include, for example, bone cement, demineralized bone matrix, hydroxyapatite and calcium phosphate materials.

Many of the above procedures are costly, require extensive healing and are not always successful; accordingly, the art field is in search of novel and improved processes and apparatuses for treating such conditions.

In view of the foregoing, it is an object of the present invention to provide an apparatus for compressing and stabilizing a patient's foot, ankle, and/or lower extremity, particularly those conditions in which internal fixation alone is insufficient. Hence, various embodiments of the present invention include external fixation in combination with internal fixation to create compression across a larger linear gap. Such combination systems and methods may be advantageous for repairing diseased bone in which large defects are present such as, for example, CN.

SUMMARY

In general, various embodiments of the present invention relate to therapeutic orthopedic devices for compressing and stabilizing a patient's foot, ankle, and/or lower extremity. In general, the various embodiments of the present invention include methods that can be used to treat a variety of maladies from diseases to fractures.

In various embodiments, a system of the present invention comprises an apparatus or device for compressing and stabilizing at least one bone in a patient's foot, ankle, and/or lower extremity, the system comprising an external fixation device, an internal fixation device, and a lower extremity stabilizer. The external fixation device is connected to the lower extremity stabilizer, and the external fixation device is adjustably connected to the internal fixation device. The internal fixation device is capable of being attached to at least one bone in a patient's foot, ankle, and/or lower extremity.

Further embodiments of the present invention also include methods for treating a malady of the foot, ankle and/or lower extremity, the malady requiring reduction of at least one bone of a patient's foot, ankle, or lower extremity. The methods comprise steps of attaching an internal fixation device to at least one bone of a patient's foot, ankle, or lower extremity; adjustably connecting an external fixation device to the internal fixation device with an adjustable member to provide compression of at least one bone and stabilizing the lower extremity of the patient with an external stabilization member, the external stabilization member being fixedly connected to the external fixation device, wherein the malady is treated. In other embodiments, methods for treating Charcot neuroarthropathy using the systems disclosed herein are described.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

The foregoing summary, as well as the following detailed description of the invention, will be better understood when read in conjunction with the appended drawings. It should be understood, however, that the invention is not limited to the precise descriptions and instrumentalities shown herein, with emphasis instead being placed upon clearly illustrating the principles of the present invention. For a more complete understanding of the present invention, and the advantages thereof, reference is now made to the following descriptions taken in conjunction with the accompanying drawings, in which.

DETAILED DESCRIPTION

Figure 1:
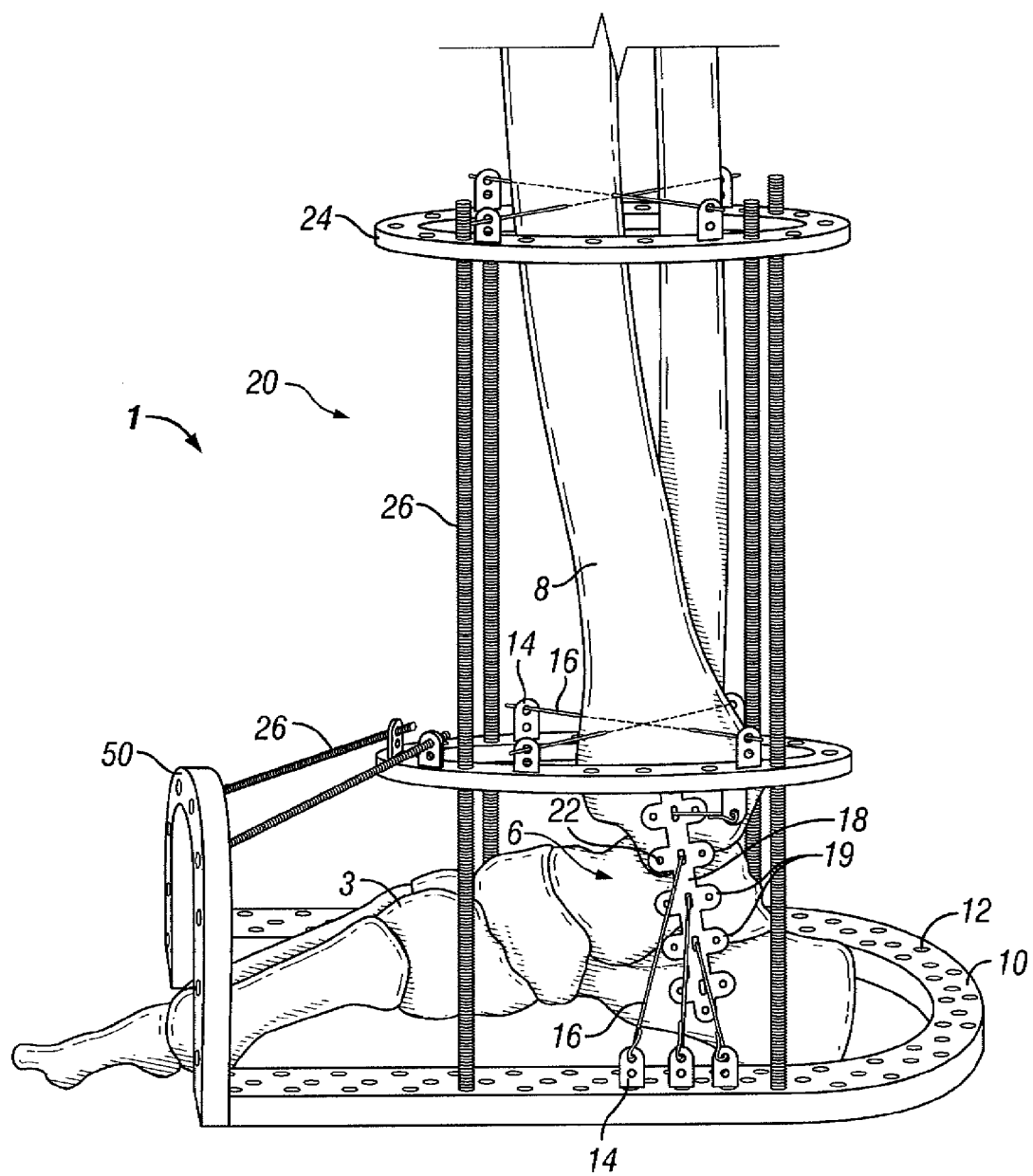
FIG. 1 is an illustration of an embodiment of a device for compressing and stabilizing a patient's foot, ankle, and/or lower extremity.

In the following description, certain details are set forth such as specific quantities, sizes, etc. so as to provide a thorough understanding of the present embodiments disclosed herein. However, it will be obvious to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing a particular embodiment of the disclosure and are not intended to be limiting thereto. Drawings are not necessarily to scale.

The following definitions and explanations are meant and intended to be controlling in any future construction unless clearly and unambiguously modified in the following description or when application of the meaning renders any construction meaningless or essentially meaningless. In cases where the construction of the term would render it meaningless or essentially meaningless, the definition should be taken from Webster's Dictionary, $3^{rd}$ Edition. Definitions and/or interpretations should not be incorporated from other patent applications, patents, or publications, related or not, unless specifically stated in this specification or if the incorporation is necessary for maintaining validity.

As used herein, the term "internal fixation device" includes devices such as, for example, at least one of wire(s), pins, nails, intramedullary nails, screws, bolts, plates, staple(s), brackets, fasteners, bars, and/or the like. Such internal fixation devices are used for stabilizing and/or compressing at least one bone in a patient's foot, ankle, and/or lower extremity. Such internal fixation devices may be constructed from a plurality of segments comprising any combination of the above components to form the complete device.

As used herein, the term "external fixation device" includes, for example, monolateral, hybrid, circular, uniplane, and bi-plane members, combinations thereof and/or the like for providing external fixation of a patient's foot, ankle and/or lower extremity. Such external fixation devices are used for stabilizing and/or compressing at least one bone in a patient's foot, ankle, and/or lower extremity.

As used herein, the term "lower extremity stabilizer or lower extremity stabilization apparatus/device" includes devices for providing stability to a patient's lower extremity, including the foot and ankle. Such lower extremity stabilizers may be connected to the above referenced internal fixation devices and external fixation devices.

As used herein, the term "radiolucent" means and refers to almost entirely transparent to radiation and/or almost entirely transparent in x-ray photographs and/or almost entirely transparent under fluoroscopy and/or other imaging modalities.

As used herein, the term "adjustably connected" refers to a connection that can be tightened or loosened.

As used herein, the term "reduce" means and refers to repair.

As used herein, the term "lower extremity" means and refers to the section of a patient's leg below the knee.

Various embodiments of the present invention generally relate to devices, systems and processes that can simultaneously reduce a malady of the foot, ankle, and/or lower extremity and provide compression and stabilization through the use of a combined internal fixation device and an external fixation device. Embodiments of the present combined system are capable of providing adequate compression in the medial, central and/or lateral columns and/or sides of the foot, ankle, and/or lower extremity, as well as the necessary stabilization for healing and/or therapy.

In some embodiments, the compression is provided by the internal fixation device and the external fixation device provides stabilization. In some other embodiments, the external fixation device provides compression and the internal fixation device provides stabilization. In still other embodiments, the compression and stabilization is provided by a combined system of the internal fixation device and the external fixation device. In still other embodiments, the internal fixation device or external fixation device alone provides the compression. In some embodiments, the internal fixation device is used alone, following an initial use of the combined system of the internal fixation device and external fixation device.

In an embodiment, the present combined system includes an internal fixation device adapted to have connectors such as, for example, transfixation wires, pins, screws or springs/spring clips fixed to it from a plurality of mounting blocks, tabs or holes on the external fixation device. Optionally, wires, pins, nails, staples, screws, bolts, plates, brackets, fasteners, bars, springs/spring clips, turnbuckles, twist locks, snap features and/or the like may extend into and/or through the bone segments in a patient's foot, ankle, and/or lower extremity. In some embodiments, the wires, pins, nails, staples, screws, bolts, plates, brackets, fasteners, bars, springs/spring clips, turnbuckles, twist locks, snap features and/or the like may be attached to the bone in such a way that they are attached substantially to the surface of the bone. Such surface attachment advantageously lowers the risk of infection in the patient.

The present combined system further includes a lower extremity stabilization assembly/device for compressing and stabilizing the foot, ankle and/or lower extremity of a patient. In some embodiments, the external fixation device and the lower extremity stabilizer are adjustably connected together. In some embodiments, the adjustable connection comprises a pivoting joint such as, for example, a ball joint. In some embodiments, the external fixation device and the lower extremity stabilizer are rigidly connected together. In other embodiments, the external fixation device and the lower extremity stabilizer are fixedly connected but capable of disengagement, such that at least one of the external fixation device and/or the lower extremity stabilizer can move relative to the other of the external fixation device or the lower extremity stabilizer. In some embodiments, a connection between the external fixation device and the lower extremity stabilizer can be adjusted to achieve compression. In some embodiments, the internal fixation device is adjustably connected to the lower extremity stabilizer. In other embodiments, the internal fixation device is rigidly connected to the lower extremity stabilizer. In embodiments wherein a rigid or fixed connection is established, the connection between components may be pre-tensioned while making the connection. For example, wires or other connectors may be stretched taut when making connections. Alternately, such connections may be tightened after connection such as with, for example, a ratchet, gears or like device.

Various embodiments of the present invention include a lower extremity stabilizer, which is any device capable of providing stabilization to a lower extremity. Suitable examples include, but are not limited to, a circumferential circular stabilizing member, a monolateral member, a hybrid member, a uniplane member, a biplane member, a combination of one or more of the aforementioned, other external fixation device configuration, and/or the like.

A combination of the internal fixation device to the external fixation device of the foot, ankle and/or the lower extremity stabilizer is a system of the present invention. In some embodiments, at least a portion of such systems are radiolucent. In other various embodiments, at least a portion of such systems have radio-opaque markings. Such properties are advantages for monitoring therapeutic progress by various imaging techniques known to those of ordinary skill in the art.

In various embodiments of the present invention, at least one of the external fixation device, the internal fixation device and the lower extremity stabilizer may comprise a material that changes dimension in response to an external stimulus. Furthermore, an adjustable member comprising the system may also comprise such materials. For example, such material may expand or contract upon exposure to temperature, standing over time, and/or interacting with ultraviolet or microwave radiation. Illustrative materials for forming these components of system include certain polymers and Nitinol (Ni—Ti alloy), for example.

In any of the various embodiments having adjustable connections, a change in compression of the combination system may be achieved by adjusting a connector interconnecting any one of the internal fixation device, external fixation device and the lower extremity stabilizer. Such connectors may include, for example, wires, threaded wires, pins, threaded pins, half pins, nails, staples, screws, bolts, plates, brackets, fasteners, bars, springs/spring clips, turnbuckles, twist locks, snap features and/or the like. Adjustment of these connectors may be performed using means known to those of ordinary skill in the relevant art. For example, in various embodiments of the invention compression may be achieved using a handheld tool (e.g., a ratchet or jig) to tighten screws or pins affixed to the combination system. Furthermore, such tightening with a handheld tool may take place while the screws or pins are attached to the internal fixation device alone (e.g., during surgery before attachment of an external fixation device). In some embodiments, an adjustable member forming the adjustable connection comprises a pivoting joint. The pivoting joint adjustable connection may be connected to at least one of the external fixation device, the internal fixation device and the lower extremity stabilizer. In various embodiments, springs or spring clips are used to apply a preloading to the adjustable member.

Advantageous features of various embodiments of the present invention include, but are not limited to, the ability to provide maximum compression and stabilization by a combination of internal and external mechanisms of action. Further, various embodiments allow for an optionally fixed configuration or a configuration which allows relative movement in various joints of the foot, ankle and/or lower extremity. In various embodiments of the invention, after adequate healing of bones has been achieved, the external fixation system is removed such that only an internal fixation device remains in a patient's foot, ankle, and/or lower extremity for prolonged compression and stabilization and, in various embodiments, maintenance of the arthrodesis site(s). In embodiments wherein the external fixation system is removed, the remaining internal fixation system provides both compression and stabilization. When the external fixation system is removed, the internal fixation system may be connected to the lower extremity stabilizer, or the internal fixation system may be unconnected. In such embodiments, the lower extremity stabilizer is an optional component.

In various embodiments, the present invention comprises an internal fixation system and an external fixation system that provides maximum compression and stabilization arthrodesis to all maladies of the foot, ankle, and/or lower extremity. In various embodiments, external threaded pins, wires, or other suitable connector means are capable of being incorporated with an internal fixation device to provide compression along a single or multiple arthrodesis site(s) across the foot, ankle, and/or lower extremity. In some embodiments, an interlocking screw is inserted within the internal fixation device to provide further stabilization. Interlocking holes of the internal fixation device, in various embodiments, also allow the insertion of compression screws initially, followed by further stabilization through attachment of externally threaded pins or other connector means that are attached to the external fixation device's foot, ankle and/or lower extremity stabilizer. In an alternate embodiment, the threaded pins or like connector means for providing compression are first used for compression via an external fixation device, and then internal screws or like connector means for providing stabilization are then applied to the internal fixation device. The threaded pins, wires or like connector means may then be secured to the external fixation device that is capable of being incorporated to the patient's foot, ankle and/or lower extremity stabilizer.

For purposes of the present disclosure, a malady of the foot, ankle, and/or lower extremity can be described as any injury, disease, or malformity, including, but not limited to Charcot neuroarthropathy, fractures, revisional foot, ankle, and/or lower extremity surgery including but not limited to malunions, nonunions, delayed unions, fibrous unions, avascular necrosis, resected osteomyelitis, incorporated autogenous and/or allogenic bone grafts for arthrodesis procedures, pseudoarthrosis and bones with decreased mineral density and cortical stiffness, congenital or acquired foot/ankle/lower extremity bone deformities (pediatric or adult), and/or the like for any reconstructive and/or elective surgery, and/or the like.

A variety of technologies are capable of use for arthrodesis for the internal fixation device and the external fixation device of the present invention. In various embodiments of the present invention, athrodesis is capable of being accomplished through the use of various connector(s)/connecting members, including, but not limited to, plates(s), intramedullary nail(s), staple(s), pin(s), bolt(s), screw(s), wire(s), fastener(s), bar(s), rail(s), spring(s)/spring clip(s), turnbuckle(s), twist lock(s), snap feature(s) and/or the like. Arthrodesis, according to various embodiments of the present invention, is capable of being accomplished through external connection of at least one bone in the foot, ankle, and/or lower extremity; or, reaming of at least one bone of the foot, ankle, and/or lower extremity; or, other internal/external connection of at least one bone of the foot, ankle, and/or lower extremity; and/or, any other means of connection common in the art for athrodesis. In various embodiments, the connecting members are adjustable connecting members.

In an embodiment, arthrodesis is accomplished through a nail adapted for insertion into the medullary canal of at least one bone of the foot, ankle, and/or lower extremity which is capable of being reamed or left unreamed. Reaming, in various embodiments, is achieved by drilling out the medullary canal of the bone with a malady, where the nail, or other structure, is inserted to stabilize and position the bone for healing. The size can vary according to at least the patient and the procedures, with an appropriate size being within the understanding of one of ordinary skill in the art.

In various embodiments, intramedullary nail systems comprise intramedullary nails having fastener holes at both the proximal and distal ends for the insertion of fasteners, or locking screws. Fasteners include all attaching means by which an implant is capable of being attached to bone. Such fasteners are capable of being inserted through a fastener hole or slot, also described as transfixation holes and screw holes.

In various embodiments, the use of locking screws is optional depending upon, for example, the severity of the bone damage and/or other factors. An intramedullary nail implanted with at least one fastener or locking screw both proximally and distally completely locks the nail in place (also known as static locking). Static locking neutralizes rotational stresses while preventing shortening of the limb. An intramedullary nail implanted with only one locking screw, either proximally or distally, partially locks the nail (also known as dynamic locking). Dynamic locking neutralizes rotational stresses on one side of the fracture site while permitting axial loading.

In various further embodiments, several nails exist with fasteners or locking screws that are much longer in shape, described as lag screws, jigs, or nail heads, which further prevent the rotation of separated bones. Other nails have spacers to absorb stress associated with repetitive, natural impact. All such devices are focused on securing bone fragments during the process of fracture healing. Other methods for attaching the nail to the bone include the use of longitudinal pins, or the use of cement injected through a cannula in a nail to secure one end to the nail.

Various types of implants and intramedullary nails exist in the prior art, each composed of different materials and having different shapes with various degrees of functionality. In various embodiments nails are formed from either a solid metal rod or a more flexible sheet metal. In alternate embodiments, nails have been proposed which form a rod material containing a central longitudinal bore disposed throughout (cannulated). Many nails have a number of longitudinal grooves cut along the rod (known as fluting), which allow for more rapid revascularization within the bone. Accordingly, nails made of various materials and those having a differing array of shapes already exist and are capable of being easily manufactured. In some embodiments of the present invention, screws with hollow bores may be used in place of intramedullary nails.

Further materials capable of use with various embodiments of the present invention include, but are not limited to nails fabricated using bioactive, biocompatible, and bioabsorbable material (e.g., bone cement, demineralized bone matrix, hydroxyapatite, and calcium phosphate). Such nails and like connectors are made from bioabsorbable polymers, copolymers, or polymer alloys that are self-reinforced containing ceramic particles or some type of reinforcement fibers. These implants and nails, as well as others, can also be made to be porous. The prior art also discloses methods to create human replica bones, grown in animals utilizing human gene technology, for ultimate use in humans, and such material is capable of being a viable supplement for standard intramedullary nails of today. Such techniques should also be considered as an appropriate part of the present invention. Likewise, in various embodiments, a system, or a portion of a system, is radiolucent or have radio-opaque markings.

Now referring to the Figures, FIG. 1 is an illustration of an embodiment of the present invention attached to a skeletal representation of a patient's foot, ankle and lower extremity. This particular embodiment of a system 1 is supporting the patient's ankle 6, foot 3, and lower extremity 8 along the medial aspect of the ankle. In general, an embodiment of a system of the present invention comprises an external fixation device 10 and a lower extremity stabilizer 20. In various embodiments, external fixation device 10 comprises at least one mounting block or mounting hole 12 for connection of at least one keeper or tab 14 and connector 16 which can be used for assisting with arthrodesis and/or compression. Threaded pins, half-pins, nuts, wires, bolts, screws, springs/spring clips, turnbuckles, twist locks, snap features and/or the like are also capable of use with various embodiments of the present invention in place of or in addition to tab 14 and connector 16 for support and/or compression.

External fixation device 10 is capable of being any shape that allows for support of the foot, ankle, and/or lower extremity. In system 1 shown in FIG. 1, the shape is that of a horseshoe wherein the horseshoe shape lies flat along the ground. Circular, rectangular, spherical and other shapes also lie within the spirit and scope of various embodiments of the present invention. Half-ring additions 50 may also be included in the external fixation device. An external fixation device of an embodiment of the present invention includes conventional constructions such as those shown in the Figures and herein described but also rail-type devices and/or external fixation device configuration(s) and other orthotic apparatuses used in foot-related procedures.

Lower extremity stabilizer 20 comprises at least one rod 26 and at least one stabilization member 24. In various embodiments, holes or mounting blocks are located along stabilization member 24 such that connector(s) 16 can be connected to tab(s) 14 to assist in arthrodesis and/or compression. Half-ring addition 50 is attached to at least one of stabilization member 24 using, for example, rods. Attachment of half-ring addition 50 may also be accomplished by other means such as, for example, pins and wires.

Still referring to FIG. 1, an internal fixation device 18 is connected to bones of foot 3, about ankle 6, and lower extremity 8 and comprises a series of sections 19 which are attached/connected to the bones through at least one screw 22. At least one connector 16 is attached from tab 14 to a section 19 of internal fixation device 18. In various embodiments, there are multiple sections 19 within internal fixation device 18. In general, internal fixation device 18 is capable of being designed for the particular bones undergoing arthrodesis, as shown in subsequent Figures hereinbelow. Various shapes of internal fixation device 18 are contemplated in the present invention including, for example, J-shape, L-shape, straight, curved and the like. Hence, the straight internal fixation device 18 in FIG. 1 should not be considered limiting. Further, in various embodiments, multiple internal fixation devices 18 may be affixed to the bones undergoing arthrodesis.

Figure 2:
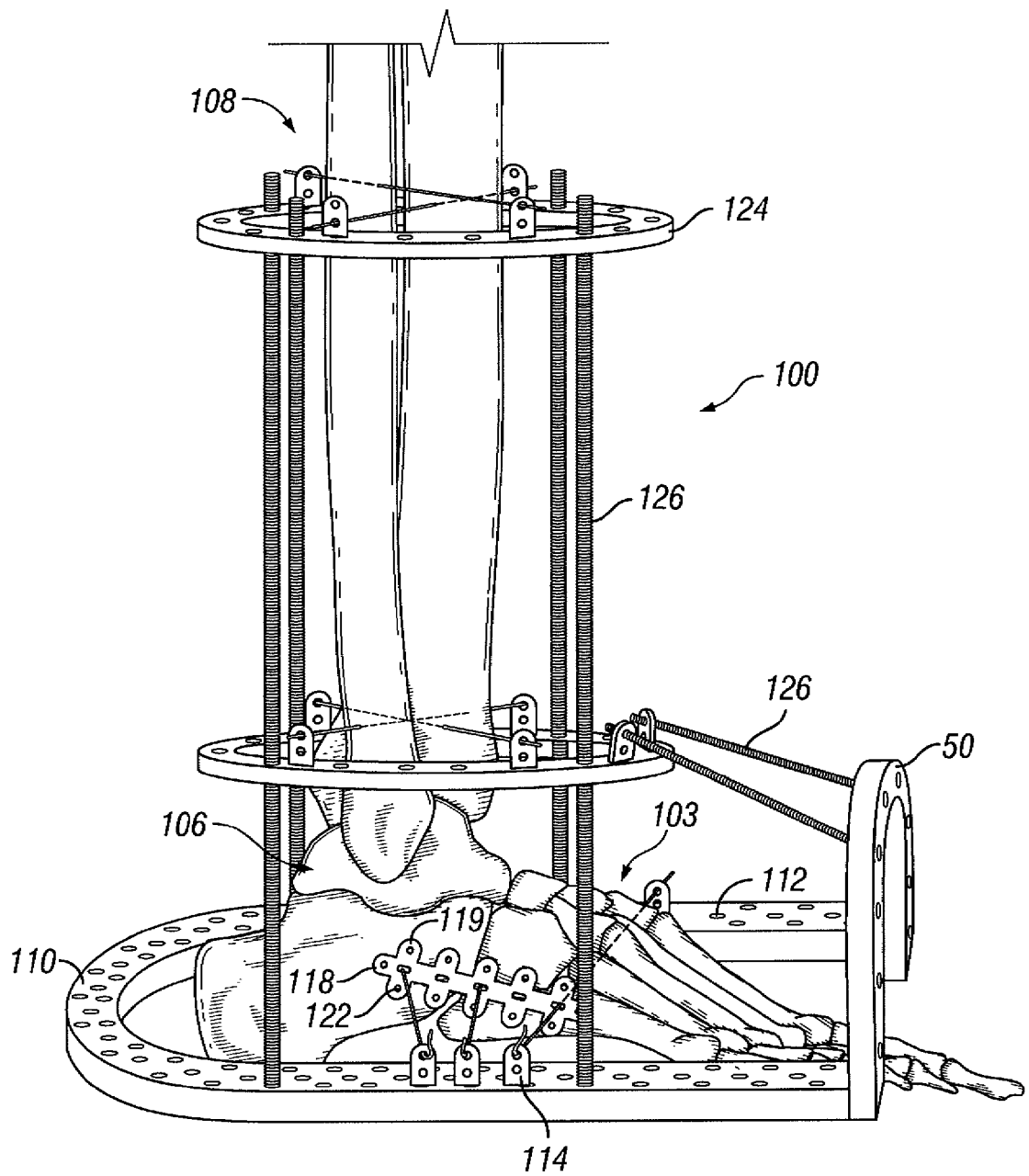
FIG. 2 is an illustration of an alternate embodiment of a device for compressing and stabilizing a patient's foot, ankle, and/or lower extremity.

Now referring to FIG. 2, a system 100, a foot 103, an ankle 106, and a portion of a lower extremity 108 are illustrated. In this alternate embodiment, an internal fixation device 118 extends along at least one bone of the lateral aspect of foot 103. Also shown in FIG. 2 are stabilization member 124, rod 126, external fixation device 110, mounting hole 112, sections 119, half-ring addition 150, screw 122 and tab(s) 114, wherein like terms are described for FIG. 1.

Figure 3A:
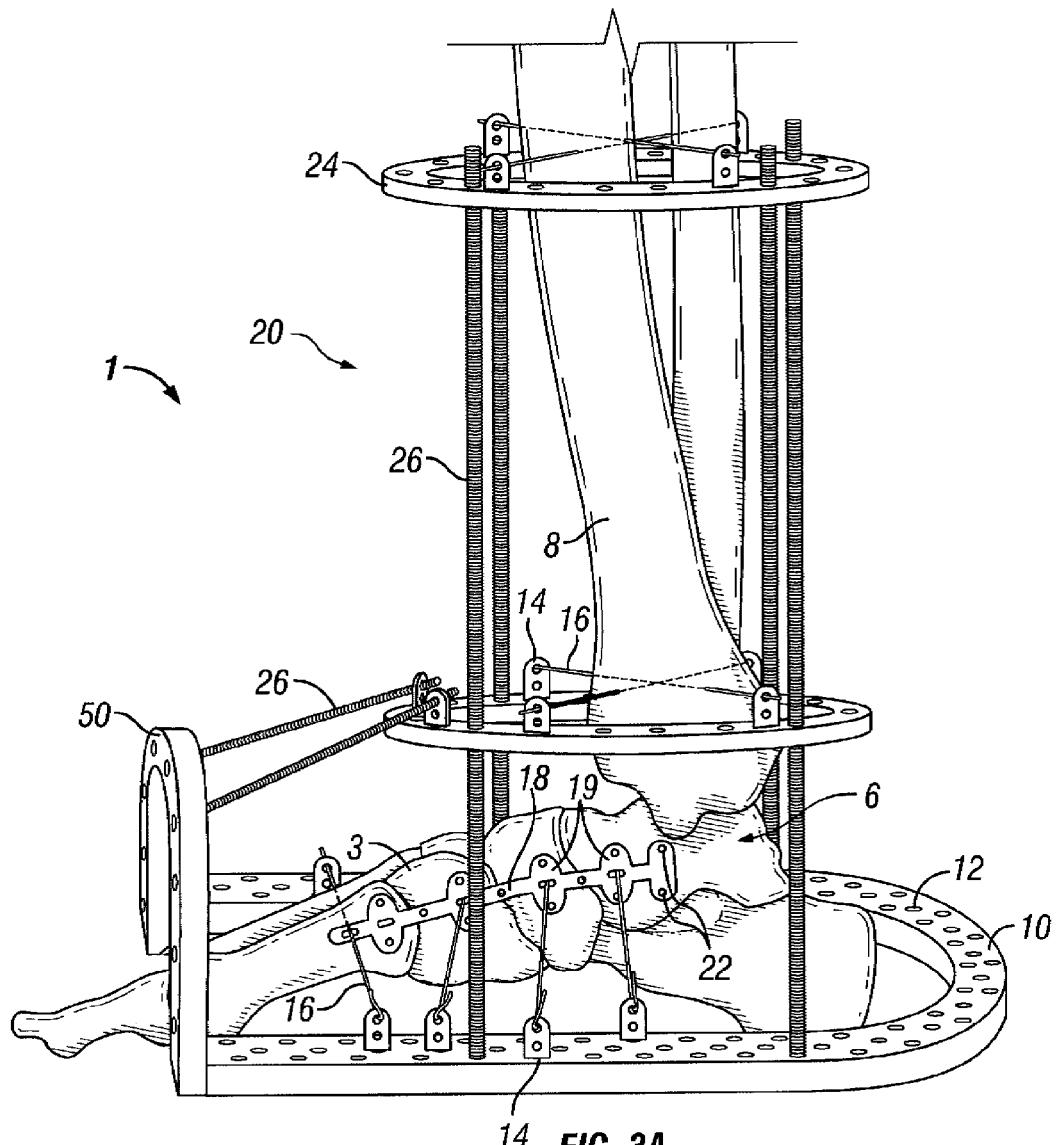
FIG. 3 is an illustration of an alternate perspective of the embodiment of FIG. 2.

Now referring to FIG. 3A, an alternative embodiment of system 1 is illustrated wherein an internal fixation device 18 is illustrated and extends along the medial aspect of at least one bone of foot 3. FIGS. 3B and 3C show expanded views of internal fixation device 18 showing attachment of screws 22. FIG. 3C shows screw holes 60 and multi-purpose hole 70, having threads 71 on one side for accommodating threaded pins or screws and non-threaded side 72 for attachment of non-threaded connectors. In some embodiments of the present invention, screws may be used in multi-purpose hole 70 and threaded pins may be used in screw holes 60. In other embodiments of the present invention, screws are used in screw holes 60, and threaded pins are used in multi-purpose hole 70. Furthermore, the diameter of screw holes 60 and multi-purpose hole 70 may vary to accommodate different sizes of threaded pins and/or screws. Multi-purpose hole 70 may also hold both a combination of pins, screws, wires and threaded pins. Hole 61 may house a screw or a pin. In some embodiments, internal fixation device 18 may be attached to foot 3 in a reversed fashion by, for example, passing connector 16 through the foot and ankle bones and attaching to external fixation device 10 on the opposite side of the foot 3.

Figure 4:
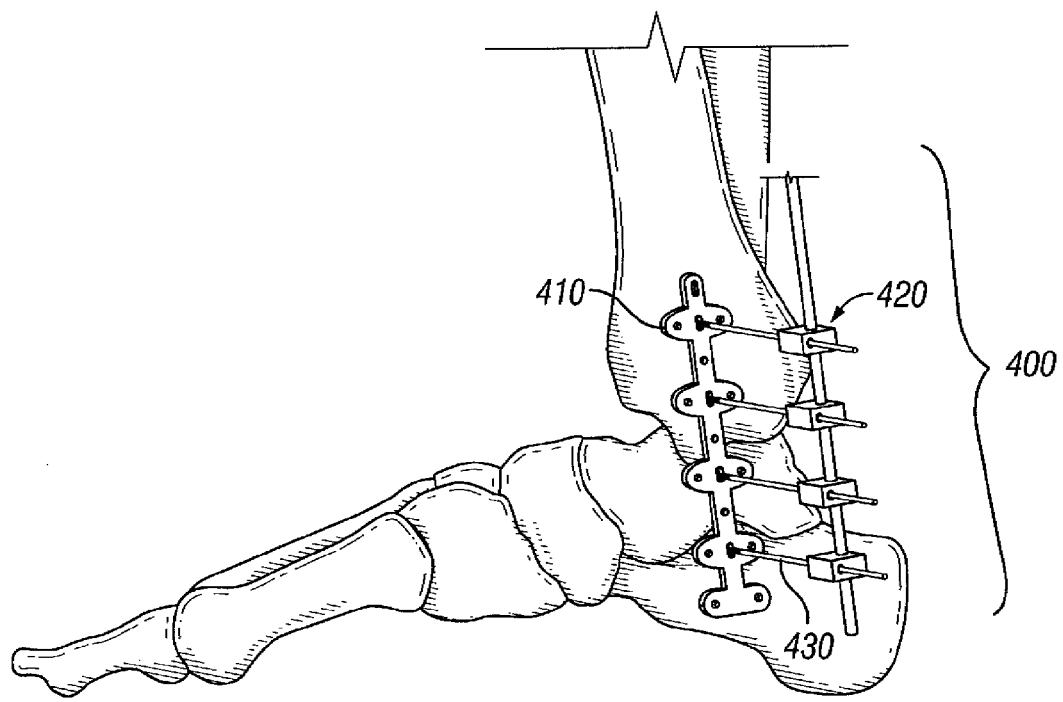
FIG. 4 is an illustration of an alternate embodiment of a device for compressing and stabilizing a patient's foot, ankle, and/or lower extremity.

Now, referring to FIG. 4, an alternate embodiment of FIG. 1 is illustrated with the use of an alternate external fixation device 400. Athrodesis is conducted along the medial ankle fusion and subtallar joint in the embodiment of FIG. 4. External fixation device 400 further includes clamp connectors 420 operable for being connected by connectors 430. An optional lower extremity stabilizer is not shown. Internal fixation device 410 is oriented as described in FIG. 1.

Figure 3A:
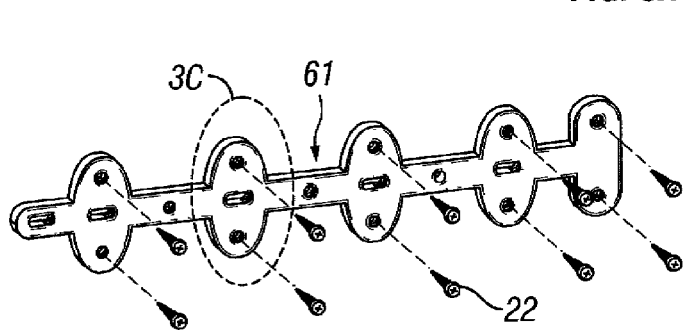
Figure 3A:
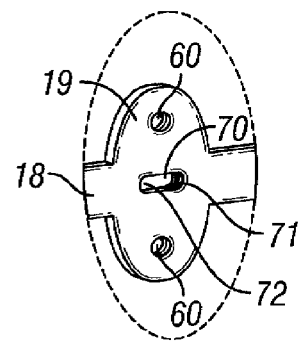
Figure 5:
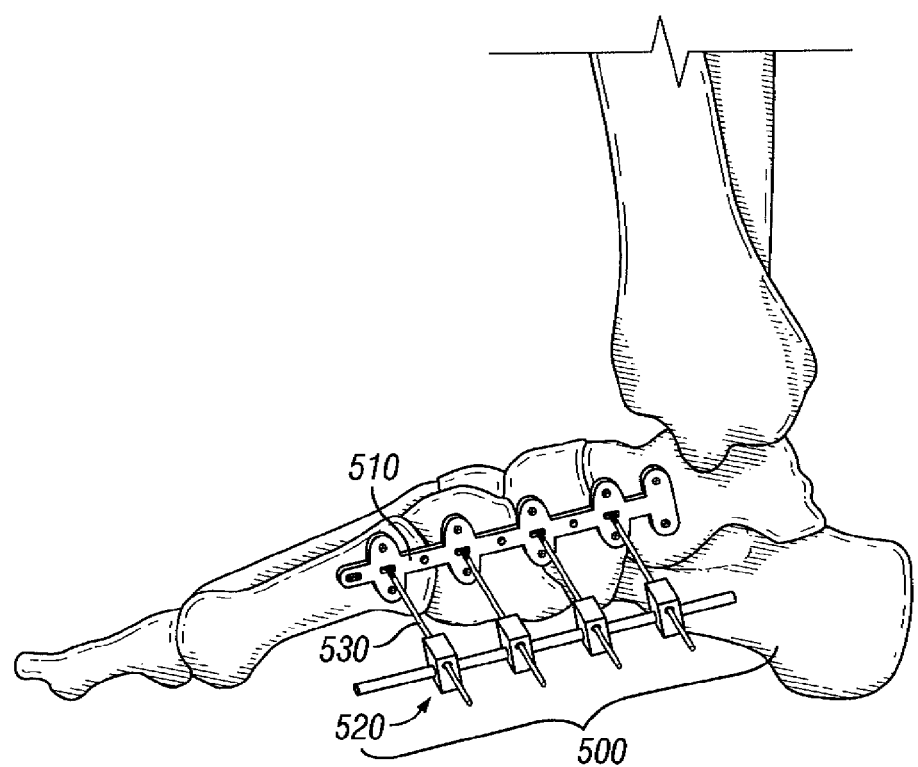
FIG. 5 is an illustration of an alternate embodiment of a device for compressing and stabilizing a patient's foot, ankle, and/or lower extremity.

Now, referring to FIG. 5, an alternate embodiment of FIG. 3 is illustrated with the use of an alternate external fixation device 500. Athrodesis is conducted along the medial aspect of the foot in the embodiment of FIG. 5. External fixation device 500 further includes clamp connectors 520 operable for being connected by connectors 530. An optional lower extremity stabilizer is not shown. Internal fixation device 510 is oriented as described in FIG. 2.

Figure 6:
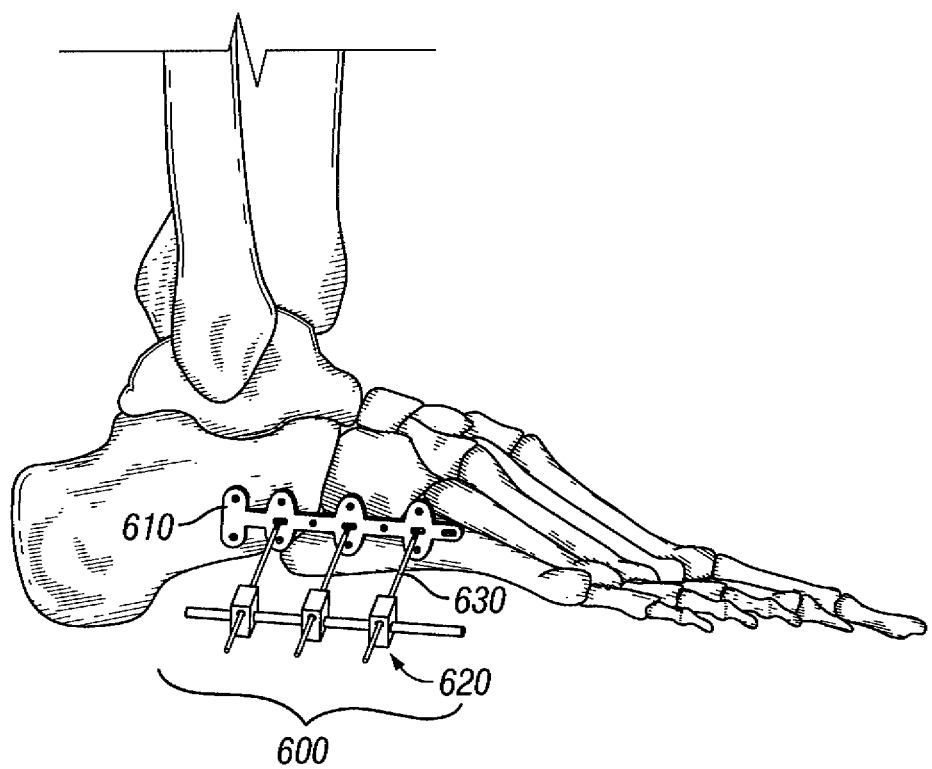
FIG. 6 is an illustration of an alternate embodiment of a device for compressing and stabilizing a patient's foot, ankle, and/or lower extremity.

Now, referring to FIG. 6, an alternate embodiment of FIG. 2 is illustrated with the use of an alternate external fixation device 600. Athrodesis is conducted along the lateral aspect of the foot in the embodiment of FIG. 5. External fixation device 600 further includes clamp connectors 620 operable for being connected by connectors 630. An optional lower extremity stabilizer is not shown. Internal fixation device 610 is oriented as described in FIG. 2.

Figure 7:
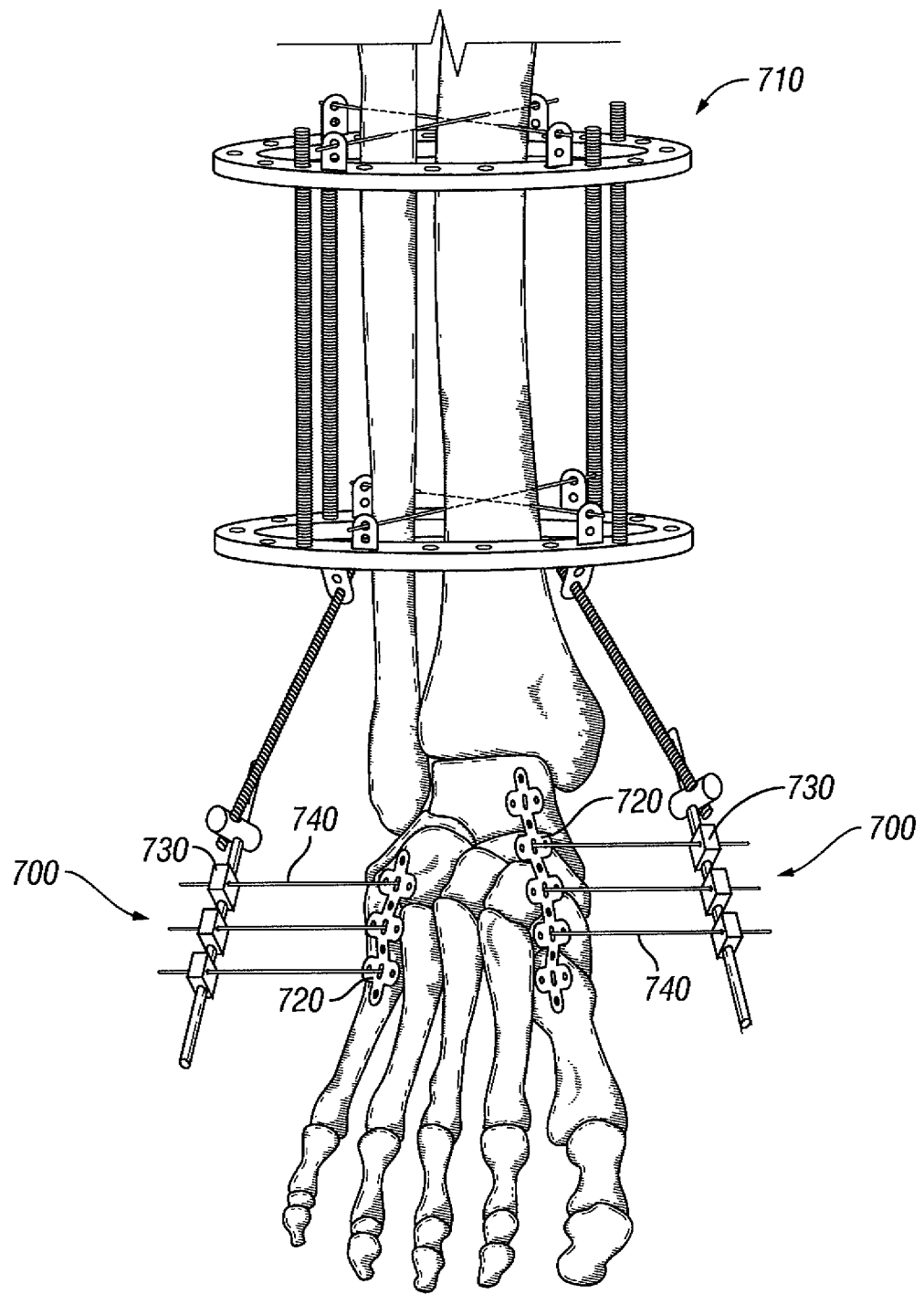
FIG. 7 is an illustration of an alternate embodiment of a device for compressing and stabilizing a patient's foot, ankle, and/or lower extremity.

Now, referring to FIG. 7, an alternate perspective of the embodiment of FIGS. 2, 3, 5 and 6 is illustrated with the use of an alternate external fixation device 700 and optional lower extremity stabilizer 710. In the embodiment shown in FIG. 7, athrodesis is conducted along the medial and lateral aspect of the foot. Two internal fixation devices 720 are oriented as described in FIG. 2. External fixation device 700 further includes clamp connectors 730 operable for being connected by connectors 740. Lower extremity stabilizer 710 is shown connected to external fixation device 700 through a threaded rod in FIG. 7. However, one of ordinary skill in the art will recognize that such connection may be made through various means including, pins and wires, for example.

Figure 8:
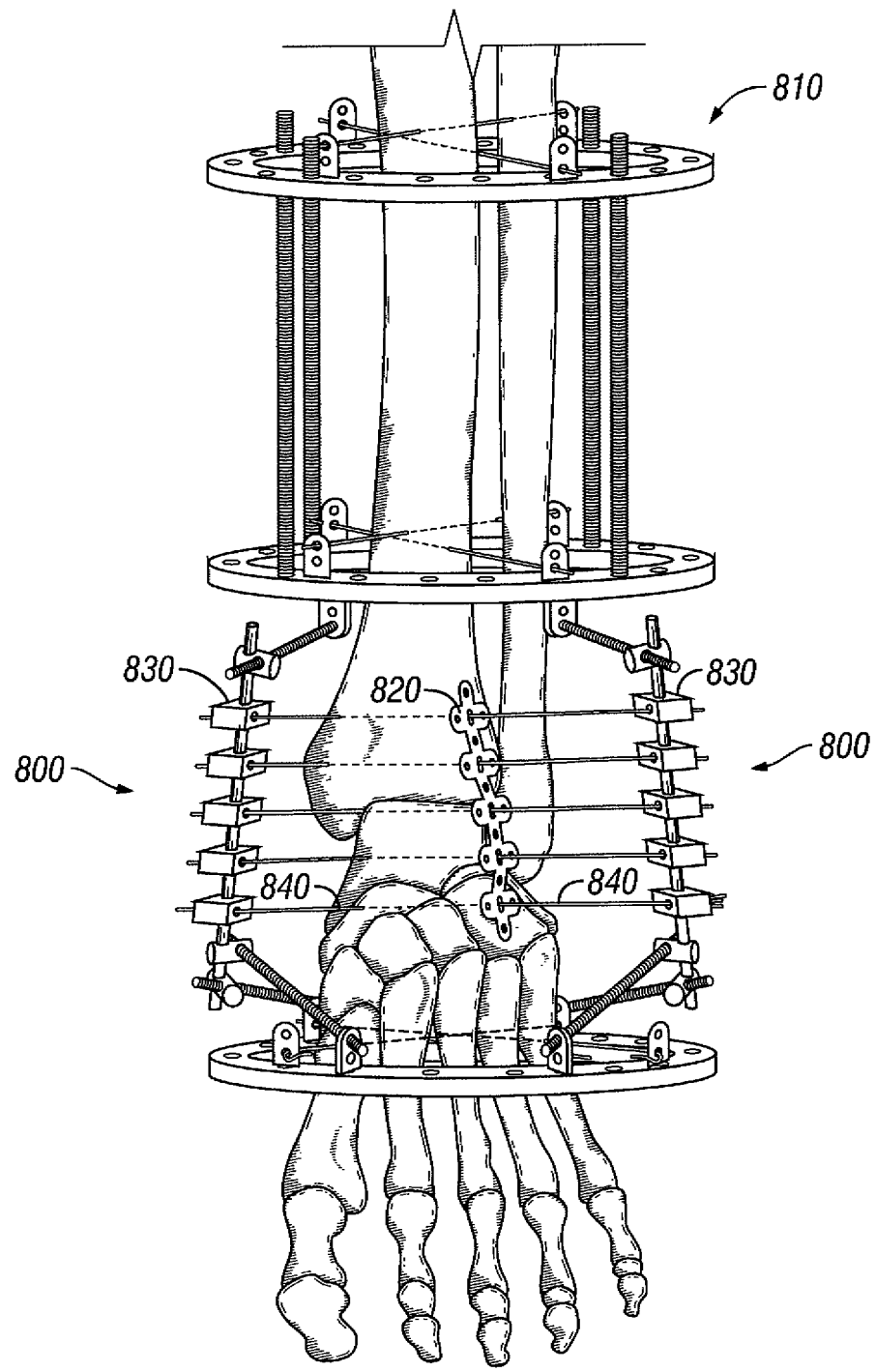
FIG. 8 is an illustration of an alternate embodiment of a device for compressing and stabilizing a patient's foot, ankle, and/or lower extremity.

Now, referring to FIG. 8, an alternate perspective of the embodiment of FIGS. 1 and 4 is illustrated with the use of an alternate external fixation device 800 and optional lower extremity stabilizer 810. In the embodiment shown in FIG. 8, athrodesis is conducted along the lateral aspect of the ankle and subtallar joint. Internal fixation device 820 is oriented as described in FIG. 1. External fixation device 800 further includes clamp connectors 830 operable for being connected by connectors 840. Lower extremity stabilizer 810 is shown connected to external fixation device 800 through a threaded rod in FIG. 8. However, one of ordinary skill in the art will recognize that such connection may be made through various means including, pins and wires, for example.

Various embodiments of the present invention also relate to methods of using systems of the present invention for treating one or more maladies of the foot, ankle, and/or lower extremity. For example, in an embodiment, Charcot neuroarthropathy may be treated using the systems described herein.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention is capable of being practiced other than as specifically described without actually departing from the spirit and scope of the present invention as defined by the appended claims.

What is claimed is:

1. A system for compressing and stabilizing at least one bone in a patient's foot, ankle, and/or lower extremity in arthrodesis, said system comprising:
   an external fixation device, wherein the external fixation device is not attached to the at least one bone in the patient's foot, ankle and/or lower extremity;
   an internal fixation device, wherein the internal fixation device attaches to the at least one bone in the patient's foot, ankle and/or lower extremity; and
   a lower extremity stabilizer, wherein the lower extremity stabilizer comprises at least one rod and at least one stabilization member, and further wherein the at least one rod and the at least one stabilization member do not attach to the at least one bone in the patient's foot, ankle and/or lower extremity; wherein said external fixation device is connected to said lower extremity stabilizer and said external fixation device is adjustably connected to said internal fixation device, and wherein the system compresses and stabilizes the at least one bone in the patient's foot, ankle and/or lower extremity and promotes arthrodesis.

2. The system of claim 1, wherein at least a portion of said system is radiolucent.

3. The system of claim 1, wherein at least a portion of said system has radio-opaque markings.

4. The system of claim 1, wherein said internal fixation device is adjustably connected to said lower extremity stabilizer.

5. The system of claim 1, wherein said internal fixation device is rigidly attached to said lower extremity stabilizer.

6. The system of claim 1, wherein said external fixation device is adjustably connected to said lower extremity stabilizer.

7. The system of claim 1, wherein an adjustable connection comprises a pivoting joint.

8. The system of claim 1, wherein at least one adjustable member comprising a pivoting joint is connected to at least one of said external fixation device, said internal fixation device, and said lower extremity stabilizer.

9. The system of claim 1, further comprising an adjustable member extending from said internal fixation device and at least one of said external fixation device and said lower extremity stabilizer.

10. The system of claim 9, wherein springs or spring clips are used to apply a preloading to the adjustable member.

11. The system of claim 9, wherein the adjustable member comprises a material that changes dimension in response to an external stimulus; wherein the change in dimension is selected from the group consisting of expansion and contraction; and wherein the external stimulus is selected from the group consisting of time, ultraviolet light exposure, microwave radiation exposure and heat exposure.

12. The system of claim 1, wherein said lower extremity stabilizer is selected from the group consisting of a circumferential circular stabilizing member, a monolateral member, a hybrid member, an uniplane member, a biplane member, and combinations thereof.

13. The system of claim 1, wherein springs or spring clips are used to apply a preloading to at least one of said lower extremity stabilizer and said external fixation device.

14. The system of claim 1, wherein at least one of said external fixation device, said internal fixation device and said lower extremity stabilizer comprise a material that changes dimension in response to an external stimulus.

15. The system of claim 14, wherein the change in dimension is selected from the group consisting of expansion and contraction.

16. The system of claim 14, wherein the external stimulus is selected from the group consisting of time, ultraviolet light exposure, microwave radiation exposure and heat exposure.

17. The system of claim 1, wherein the external fixation device is adjustably connected to the internal fixation device by a connector.

* * * * *